US00RE40534E

(19) United States
(12) Reissued Patent
Harrison et al.

(10) Patent Number: US RE40,534 E
(45) Date of Reissued Patent: Oct. 7, 2008

(54) CLEAR CONDITIONING DETERSIVE COMPOSITIONS CONTAINING POLYSILOXANES WITH AT LEAST ONE CYCLIC SIDE CHAIN

(75) Inventors: James Jeffries Harrison, West Hills, CA (US); Zimming Sun, Fountain Valley, CA (US); James Parr, San Juan Capistrano, CA (US); Nohemi Harrison, West Hills, CA (US)

(73) Assignee: Chemsil Silicones, Inc., Chatsworth, CA (US)

(21) Appl. No.: 11/203,649

(22) Filed: Aug. 12, 2005

Related U.S. Patent Documents

Reissue of:
(64) Patent No.: 6,605,577
Issued: Aug. 12, 2003
Appl. No.: 10/022,042
Filed: Dec. 17, 2001

U.S. Applications:
(63) Continuation-in-part of application No. 10/056,964, filed on Nov. 7, 2001, now Pat. No. 6,642,194.

(51) Int. Cl.
*C11D 9/36* (2006.01)

(52) U.S. Cl. ..... 510/122; 510/119; 510/276; 510/287; 510/308; 510/466; 510/515

(58) Field of Classification Search ..... 510/119, 510/276, 287, 308, 466, 515
See application file for complete search history.

(56) References Cited

U.S. PATENT DOCUMENTS

| | | | | |
|---|---|---|---|---|
| 3,957,970 | A | | 5/1976 | Korkis |
| 3,964,500 | A | | 6/1976 | Drakoff |
| 4,059,581 | A | * | 11/1977 | Prokai ..... 544/69 |
| 4,364,837 | A | | 12/1982 | Pader |
| 4,749,565 | A | | 6/1988 | Grollier |
| 4,927,898 | A | * | 5/1990 | King et al. ..... 528/27 |
| 5,275,761 | A | | 1/1994 | Bergmann |
| 5,277,968 | A | | 1/1994 | Canivenc |
| 5,306,434 | A | | 4/1994 | Schueller et al. |
| 5,358,667 | A | | 10/1994 | Bergmann |
| 5,389,364 | A | | 2/1995 | Cifuentes et al. |
| 5,409,695 | A | | 4/1995 | Abrutyn et al. |
| 5,415,857 | A | | 5/1995 | Robbins et al. |
| 5,456,863 | A | | 10/1995 | Bergmann |
| 5,474,712 | A | | 12/1995 | Dotolo et al. |
| 5,540,952 | A | * | 7/1996 | Canivenc et al. ..... 427/387 |
| 5,807,956 | A | | 9/1998 | Czech |
| 5,981,681 | A | | 11/1999 | Czech |
| 6,011,126 | A | | 1/2000 | Dubief et al. |
| 6,040,288 | A | | 3/2000 | Popoff et al. |
| 6,086,862 | A | | 7/2000 | Dubief et al. |
| 6,090,376 | A | | 7/2000 | Dubief et al. |
| 6,143,286 | A | | 11/2000 | Bhambhani et al. |
| 6,162,423 | A | | 12/2000 | Sebag et al. |
| 6,174,522 | B1 | | 1/2001 | Baravetto et al. |
| 6,180,576 | B1 | | 1/2001 | Melby et al. |
| 6,194,363 | B1 | | 2/2001 | Murray |
| 6,200,554 | B1 | | 3/2001 | Yeoh et al. |

FOREIGN PATENT DOCUMENTS

| | | |
|---|---|---|
| EP | 0407042 | 1/1991 |
| JP | 6-321742 | 11/1994 |
| WO | WO 96/32092 | 10/1996 |

* cited by examiner

*Primary Examiner*—Charles I Boyer
(74) *Attorney, Agent, or Firm*—Stout, Uxa, Buyan & Mullins, LLP; Frank J. Uxa; Carlos A. Fisher

(57) ABSTRACT

This invention relates to a clear shampoo comprising a polysiloxane component and methods for making the same. In one embodiment, the polysiloxane component comprises a side chain component having a hindered amine group.

38 Claims, No Drawings

CLEAR CONDITIONING DETERSIVE COMPOSITIONS CONTAINING POLYSILOXANES WITH AT LEAST ONE CYCLIC SIDE CHAIN

Matter enclosed in heavy brackets [ ] appears in the original patent but forms no part of this reissue specification; matter printed in italics indicates the additions made by reissue.

This application is a continuation-in-part of U.S. patent application Ser. No. 10/056,964, filed Nov. 7, 2001 *now U.S. Pat. No. 6,642,194*, the disclosure of which is incorporated in its entirety herein by reference.

BACKGROUND OF THE INVENTION

The concept of cleansing and conditioning detersive products has drawn great attention since its launch in the early 1980's. From a technical point, cleansing and conditioning are contradictions, since conditioning has to deposit some ingredients on an object and cleansing has to remove the deposited ingredients from the object. To combine cleansing and conditioning in detersive products means when the product removes the dirt from the object, the product also simultaneously deposits some conditioning ingredients on the object. The conditioning effects depend on the equilibrium between the removed dirt, conditioning ingredient and deposit conditioning ingredients. For hair products, conditioning involves depositing certain agents onto the hair to give it the protection, softness, shine and detangling effects. Less deposition means less conditioning and more deposition means more conditioning or over conditioning.

To achieve proper conditioning formulations, chemists are faced with the challenge of choosing the appropriate conditioning ingredients, the proper ratio of conditioning ingredients to surfactants and methods of incorporating conditioning ingredients into the detersive system to form stable products.

A conditioning ingredient should have the basic characteristic of being water-insoluble, easy to be spread and have some affinities with the application objects. Polysiloxane, such as dimethicone, and derivatives are water-insoluble and are widely used conditioning ingredients. Furthermore, polysiloxanes usually give good hair protection, softening, shine and detangling effects.

The various technical methods for incorporating polysiloxanes, such as dimethicone, into the detersive products have been patented. The focus is on the particle size distribution of dimethicone surfactant emulsion and stability of the shampoo. Smaller particle size means more stability and more deposition to the targeted object.

Although some success has been achieved in being able to incorporate polysiloxanes, such as dimethicones, into detersive compositions, other challenges still remain. It remains a challenge to be able to formulate a stable conditioning/detersive composition, especially when a polysiloxane (e.g. dimethicone) is employed. Considering the regular viscosity of the detersive composition and the relatively lightweight of the conditioning ingredients, it is very difficult to achieve a long-term stability of the products. For example, the products tend to separate with the conditioning ingredients settling on top of the water-detergent solution. Furthermore, it remains a challenge to be able to formulate a clear stable conditioning/detersive composition, especially when the conditioning ingredient is a polysiloxane.

There continues to be a need to have a more stable formulation having a conditioner and a detersive composition. In particular, there is a need to have a clear detersive formulation which comprises a polysiloxane.

SUMMARY OF THE INVENTION

The present invention meets this need and provides for a stable, clear detersive composition having a polysiloxane component. In one embodiment, the present invention provides for a clear detersive composition comprising a conditioner. A clear conditioning/detersive composition includes, for example, a conditioning shampoo which is substantially clear.

The term "clear" as used herein means a substantial amount of light may pass through. Alternatively, the term "clear" means transparent or translucent, as opposed to opaque.

In accordance with the invention, a composition comprising an emulsifier component and a polysiloxane component is provided. The polysiloxane component comprises at least one side chain component A having the general formula:

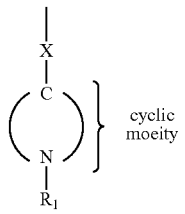

R1 is an H, OH, or a C1–C5 hydrocarbon; X is a C1–C10 hydrocarbon, a heteroatom or

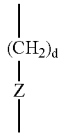

Z is a heteroatom and d is 0 to about 6.

Further in accordance with the present invention, the composition further comprises a detersive component. For example, the composition comprises about 5% to about 60% of the detersive component, about 0.01% to about 10% of the emulsifier component, and about 0.01% to about 10% of the polysiloxane component.

Still further in accordance with the present invention, a method of making a clear shampoo is provided. The method comprises the steps of forming a micro-emulsion of a polysiloxane component, and combining the micro-emulsion with a detersive component. The micro-emulsion is formed by combining a non-ionic emulsifier with a polysiloxane component.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

The present invention is, in part, based upon the surprising discovery that a polysiloxane component may be combined with a detersive component to form a clear composition, preferably a clear shampoo. In a broad embodiment, the composition comprises an emulsifier component and a polysiloxane component.

Without wishing to limit the invention to any theory or mechanism of operation, it is believed that a clear composition, for example, a clear shampoo composition, may be produced by combining a detersive component with performed micro emulsion comprising a polysiloxane component. The micro emulsions may or may not remain intact after it is combined with a detersive component.

In one embodiment, a composition of the present invention remains stable (for example remain clear) for about 360 days after manufacturing.

In one embodiment, the micro emulsions are formed by mixing the emulsifier components with the polysiloxane components, preferably in the presence of water. For example, micro emulsion are formed by homogenizing emulsifier components with polysiloxane components in a tank at about 40 to about 70 degrees C. In one embodiment, a homogenizer employed is model number ME 100 LC by Charles Ross and Son, Hauppauga, N.Y. In one embodiment, the ratio (by weight) of the emulsifier component to the polysiloxane component in a micro emulsion is about 1:1, 1:2, 1:3, or 1:4.

In one embodiment, emulsifier components include a non-ionic emulsifier. In another embodiment, the emulsifier components include a non-ionic emulsifier and at least one of an anionic emulsifier and an amphoteric emulsifier. The anionic amphoteric emulsifiers are selected from the anionic and amphoteric surfactants, respectively.

Non-limiting examples of non-ionic surfactants include: Capryleth-n, where n=4, 5; Deceth-n, where n=3, 4, 5, 6, 8, 9, 10; Undeceth-n, where n=3, 5, 7, 8, 9, 11; Coceth-n, where n=3, 5, 7, 8, 10; C9–11 Pareth-n, where n=5, 6, 8; C9–15 Pareth-8; C11–15 Pareth-n, where n=3, 5, 9, 12, 15, 20, 30, 40; C11–21-Pareth-n, where n=3, 10; C12–1–n, where n=3, 5, 7, 9, 12; C12–14 Pareth-n, where n=5, 7, 9, 12; C12–15 Pareth-n, where n=2, 3, 4, 5, 7, 9, 10, 11, 12; C12–16 Pareth-n, where n=5, 7, 9; C14–15 Pareth-n, where n=4, 7, 8, 11, 12, 13; C20–22 Pareth-30; C20–40 Pareth-n, where n=3, 10, 24, 40; C22–24 Pareth-33; C30–50 Pareth-n, where n=3, 10, 40; C40–60 Pareth-n, where n=3, 10; C12–14 Sec-Pareth-5; C12–14 Sec-Pareth-n, where n=8, 9, 15, 20, 30, 40, 50; C11–15 Sec-Pareth-12; Dihydrocholeth-n, n=15, 20, 30; Glycereth-n, where n=7, 12, 20, 26, 31; Hydrogenated Talloweth-n, where n=12, 25; Isoceteth-n, where n=10, 15, 20, 30; Isodeceth-n, where n=4, 5, 6; Isolaureth-n, where n=3, 6, 10; Isostearetn-n, where n=2, 3, 10, 12, 20, 22, 25, 50; Laneth-n, where n=5, 10, 15, 16, 20, 25, 40, 50, 60, 75; Laureth-n, where n=1, 2, 3, 4, 5, 6, 7, 8, 9, 10, 11, 12, 13, 14, 15, 16, 20, 21, 23, 25, 30, 40, 50; Myreth-n, where n=2, 3, 4, 5, 10; Octyldodeceth-n, where n=5, 10, 16, 20, 25, 30; Oleth-n, where n=2, 4, 5, 6, 7, 8, 9, 10, 11, 12, 15, 16, 20, 23, 24, 25, 30, 35, 40, 44, 50, 106; PPG-2-Ceteareth-9; PPG-4-Ceteareth-12; PPG-10-Ceteareth-20; PPG-1-Ceteth-n, where n=1, 5, 10, 20; PPG-2-Ceteth-n, where n=1, 5, 10, 20; PPG-2-Ceteth-n, where n=5, 10, 20; PPG-4-Ceteth-n, where n=1, 5, 10, 20; PPG-5-Ceteth-20; PPG-8-Ceteth-n, where n=1, 2, 5, 10; PPG-n Cetyl Ether, where n=10, 20, 28, 30, 50; PPG-2 C12–15 Pareth-6; PPG-4 C13–15 Pareth-15; PPG-5 C9–15 Pareth-6; PPG-6 C9–11 Pareth-n, where n=5, 12, 11; PPG-3 C12–14 Sec-Pareth-7; PPG-4 C12–14 Sec-Pareth-5; PPG-5 C12–14 Sec-Pareth-7; PPG-5 C12–14 Sec-Pareth-9; PPG-1-Deceth-6; PPG-2-Deceth-10; PPG-4-Deceth-n, where n=4, 6; PPG-6-Deceth-n, where n=4, 9; PPG-8 Deceth-6; PPG-14 Deceth-6; PPG-6-Decyltetradeceth-n, where n=12, 20, 30; PPG-13 Decyltetradeceth-24; PPG-20-Decyltetradeceth-10; PPG-9-Ethylhexeth-5; PPG-20-Glycereth-30; PPG-24-Glycereth-24; PPG-66-Glycereth-12; PPG-2-Isodeceth-n, where n=4, 6, 9, 12; PPG-3-Isodeceth-n, where n=1, 9; PPG-3-Isostearetn-9; PPG-12-Laneth-50; PPG-3-Laureth-9; PPG-4 Laureth-n, where n=2, 5, 7; PPG-6-Laureth-3; PPG-25-Laureth-25; PPG-9-Steareth-3; PPG-23-Steareth-34; PPG-30 Steareth-4; PPG-34-Steareth-3; PPG-1 Trideceth-6; PPG-4 Trideceth-6; PPG-6 Trideceth-8; Sorbeth-n, where n=6, 20, 30, 40; Tocophereth-n, where n=5, 10, 12, 18, 50; Trideceth-n, where n=2, 3, 5, 6, 7, 8, 9, 10, 11, 12, 15, 18, 20, 21, 50; Ceteth-n, where n=1, 2, 3, 4, 5, 6, 7, 10, 12, 14, 15, 16, 17, 18, 20, 23, 24, 25, 30, 40, 45; Ceteareth-n, where n=3, 4, 5, 6, 7, 8, 9, 10, 11, 12, 13, 14, 15, 16, 17, 18, 20, 22, 23, 24, 25, 27, 28, 29, 30, 33, 34, 40, 50, 55, 60, 80, 100; Cetoleth-n, where n=6, 10, 11, 15, 20, 22, 24, 25, 30; Choleth-n, where n=5, 10, 15, 20, 24, 30; Steareth-n, where n=2, 3, 4, 5, 6, 7, 8, 10, 11, 13, 14, 15, 16, 20, 21, 25, 27, 30, 40, 50, 80, 100; and Beheneth-n, where n=5, 10, 20, 25, 30.

Non-limiting examples of anionic surfactants which may be employed as emulsifiers include: Alkyl ether sulfates, Alkyl sulfates, α-Olefin sulfonates, sulfocuccinates, Alkyl isethionates, Acyl amides, Acyl peptides, Alkyl ether carboxylates, Alkyl phosphates, Acylamphoglycinates, Acylamphopropionates and Amine oxides, Ammonium C12–15 Alkyl Sulfate, Ammonium Capryleth Sulfate, Ammonium Coco-Sulfate, Ammonium C12–15 Pareth Sulfate, Ammonium Laureth-n Sulfate, where n=3, 5, 7, 9, 12; Ammonium Lauryl Sulfate, Ammonium Myreth Sulfate, Ammonium Myristyl Sulfate, Ammonium Nonoxynol-4 Sulfate, Ammonium Nonoxynol-30 Sulfate, DEA-C12–13 Alkyl Sulfate, DEA-C12–15 Alkyl Sulfate, DEA-Cetyl Sulfate, DEA-C12–13 Pareth-3 Sulfate, DEA-Laureth Sulfate, DEA-Lauryl Sulfate, DEA-Myreth Sulfate, DEA-Myristyl Sulfate, Magnesium Coco-Sulfate, Magnesium Laureth-n Sulfate, where n=2, 5, 8, 16; Magnesium Lauryl Sulfate, Magnesium Myreth Sulfate, Magnesium Oleth Sulfate, Magnesium PEG-3 Cocamide Sulfate, Magnesium Sulfate, Magnesium/TEA-Coco-Sulfate, MEA-Laureth Sulfate, MEA-Lauryl Sulfate, MIPA C12–15 Pareth Sulfate, MIPA-Laureth Sulfate, MIPA-Lauryl Sulfate, Mixed Isopropanolamines Lauryl Sulfate, Potassium Glycol Sulfate, Potassium Lauryl Sulfate, Potassium Persulfate, Potassium Sulfate, Protamine Sulfate, Sodium C8–10 Alkyl Sulfate, Sodium C12–13 Alkyl Sulfate, Sodium C12–15 Alkyl Sulfate, Sodium C12–18 Alkyl Sulfate, Sodium C16–20 Alkyl Sulfate, Sodium Cellulose Sulfate, Sodium Cetearyl Sulfate, Sodium Cetyl Sulfate, Sodium Cholesteryl Sulfate, Sodium Chondroitin Sulfate, Sodium Coceth Sulfate, Sodium Coceth-30 Sulfate, Sodium Coco/Babassu Sulfate, Sodium Coco/Hydrogenated Tallow Sulfate, Sodium Cocomonoglyceride Sulfate, Sodium Coco-Sulfate, Sodium C9–15 Pareth-3 Sulfate, Sodium C10–15 Pareth Sulfate, Sodium C12–13 Pareth Sulfate, Sodium C12–15 Pareth Sulfate, Sodium C13–15 Pareth-3 Sulfate, Sodium C12–14 Sec-Pareth Sulfate, Sodium Cyclodextrin Sulfate, Sodium Deceth Sulfate, Sodium Decyl Sulfate, Sodium Dermatan Sulfate, Sodium Dextran Sulfate, Sodium Dicocoylethylenediamine PEG-15 Sulfate, Sodium Ethylhexyl Sulfate, Sodium Laneth Sulfate, Sodium Laureth Sulfate, where n=2, 2, 5, 7, 8, 12, 40; Sodium Lauryl Sulfate, Sodium/MEA-PEG-3 Cocamide Sulfate, Sodium Myreth Sulfate, Sodium Myristyl Sulfate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8

Sulfate, Sodium Nonoxynol-10 Sulfate, Sodium Nonoxynol-25 Sulfate, Sodium Octoxynol-2 Sulfate, Sodium Octoxynol-6 Sulfate, Sodium Octoxynol-9 Sulfate, Sodium Oleth Sulfate, Sodium Oleyl Sulfate, Sodium Stearoyl Chondroitin Sulfate, Sodium Stearyl Sulfate, Sodium Sucrose Octasulfate, Sodium Tallow Sulfate, Sodium Trideceth Sulfate, Sodium Tridecyl Sulfate, TEA-C10–15 Alkyl Sulfate, TEA-C12–13 Alkyl Sulfate, TEA-C12–14 Alkyl Sulfate, TEA-C12–15 Alkyl Sulfate, TEA-Coco-Sulfate, TEA-C12–13 Pareth-3 Sulfate, TEA-Laneth-5 Sulfate, TEA-Laureth Sulfate, TEA-Lauryl Sulfate, TEA-Oleyl Sulfate, TEA-PEG-3 Cocamide Sulfate, TIPA-Laureth Sulfate, TIPA-Lauryl Sulfate, Ammonium C9–10 Perfluorosulfonate, Ammonium Cumenesulfonate, Ammonium Dodecylbenzenesulfonate, Ammonium Xylenesulfonate, Calcium Dodecylbenzenesulfonate, Calcium Lignosulfonate, Calcium Pantetheine Sulfonate, Cocamidopropyl Dimethylammonium C8–16 Isoalkylsuccinyl Lactoglobulin Sulfonate, DEA-Dodecylbenzenesulfonate, DEA-Methyl Myristate Sulfonate, Disodium Bisethylphenyl Triaminotriazine Stilbenedisulfonate, Disodium Cetyl Phenyl Ether Disulfonate, Disodium Cocoamphocarboxyethylhydroxypropylsulfonate, Disodium Decyl Phenyl Ether Disulfonate, Disodium Distyrylbiphenyl Disulfonate, Disodium Lauriminobishydroxypropylsulfonate, Disodium Lauryl Phenyl Ether Disulfonate, Disodium Methylene Dinaphthalenesulfonate, Isopropylamine Dodecylbenzenesulfonate, Magnesium Lauryl Hydroxypropyl Sulfonate, MIPA-Dodecylbenzenesulfonate, Potassium Cumenesulfonate, Potassium Dodecylbenzenesulfonate, Potassium Lauryl Hydroxypropyl Sulfonate, Potassium Phenylbenzimidazole Sulfonate, Potassium Toluenesulfonate, Potassium Xylene Sulfonate, Sodium Benzotriazolyl Butylphenol Sulfonate, Sodium C13–17 Alkane Sulfonate, Sodium C14–18 Alkane Sulfonate, Sodium C9–22 Alkyl Sec Sulfonate, Sodium C14–17 Alkyl Sec Sulfonate, Sodium Caproamphohydroxypropylsulfonate, Sodium Capryloamphohydroxy-propylsulfonate, Sodium Caprylyl Sulfonate, Sodium C8–16 Isoalkylsuccinyl Lactoglobulin Sulfonate, Sodium Cocoamphohydroxypropylsulfonate, Sodium Cocoglyceryl Ether Sulfonate, Sodium Cocomonoglyceride Sulfonate, Sodium C12–14 Olefin Sulfonate, Sodium C14–16 Olefin Sulfonate, Sodium C14–18 Olefin Sulfonate, Sodium C16–18 Olefin Sulfonate, Sodium C14–15 Pareth-PG Sulfonate, Sodium C12–15 Pareth-3 Sulfonate, Sodium C12–15 Pareth-7 Sulfonate, Sodium C12–15 Pareth-15 Sulfonate, Sodium Cumenesulfonate, Sodium Decylbenzenesulfonate, Sodium Dodecylbenzenesulfonate, Sodium Guaiazulene Sulfonate, Sodium Hexyldiphenyl Ether Sulfonate, Sodium Hydroxymethane Sulfonate, Sodium Lauroamphohydroxypropylsulfonate, Sodium Lignosulfonate, Sodium Methylnaphthalenesulfonate, Sodium Naphthalenesulfonate, Sodium Naphthol Sulfonate, Sodium m-Nitrobenzenesulfonate, Sodium Octoxynol-2 Ethane Sulfonate, Sodium Oleoamphohydroxypropylsulfonate, Sodium Palm Glyceride Sulfonate, Sodium Pantetheine Sulfonate, Sodium Phenolsulfonate, Sodium Phenylbenzimidazole Sulfonate, Sodium Polydimethylglycinophenolsulfonate, Sodium Polynaphthalenesulfonate, Sodium Polystyrene Sulfonate, Sodium Shale Oil Sulfonate, Sodium Stearoamphohydroxypropylsulfonate, Sodium Stearoxy PG-Hydroxyethylcellulose Sulfonate, Sodium Toluenesulfonate, Sodium Tridecylbenzenesulfonate, Sodium Xylenesulfonate, TEA-Dodecylbenzenesulfonate, TEA-Phenylbenzimidazole Sulfonate, TEA-Tridecylbenzenesulfonate, Ammonium Lauryl Sulfosuccinate, Cholesteryl C16–18 Alkenyl Succinate, Decyl Succinate, Diammonium Lauramido-MEA Sulfosuccinate, Diammonium Lauryl Sulfosuccinate, Diammonium Oleamido PEG-2 Sulfosuccinate, Diamyl Sodium Sulfosuccinate, Dicapryl Sodium Sulfosuccinate, Dicyclohexyl Sodium Sulfosuccinate, Diethoxyethyl Succinate, Diethylhexyl Sodium Sulfosuccinate, Diethylhexyl Succinate, Diethyl Succinate, Diglycol Guanidine Succinate, Diheptyl Sodium Sulfosuccinate, Disodium Cetearyl Sulfosuccinate, Disodium Cocamido MEA-Sulfosuccinate, Disodium Cocamido MIPA-Sulfosuccinate, Disodium Cocamido PEG-3 Sulfosuccinate, Disodium Coco-Glucoside Sulfosuccinate, Disodium Cocoyl Butyl Gluceth-10 Sulfosuccinate, Disodium C12–15 Pareth Sulfosuccinate, Disodium C12–14 Sec-Pareth Sulfosuccinate, Disodium C12–14 Sec-Pareth-5 Sulfosuccinate, Disodium C12–14 Sec-Pareth-7 Sulfosuccinate, Disodium C12–14 Sec-Pareth-9 Sulfosuccinate, Disodium C12–14 Sec-Pareth-12 Sulfosuccinate, Disodium Cystinyl Disuccinate, Disodium Deceth-5 Sulfosuccinate, Disodium Deceth-6 Sulfosuccinate, Disodium Dimethicone Copolyol Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Laneth-5 Sulfosuccinate, Disodium Lauramido MEA-Sulfosuccinate, Disodium Lauramido PEG-2 Sulfosuccinate, Disodium Lauramido PEG-5 Sulfosuccinate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleth-3 Sulfosuccinate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-5 Laurylcitrate Sulfosuccinate Disodium PEG-8 Palm Glycerides Sulfosuccinate Disodium PEG-8 Ricinosuccinate, Disodium Ricinoleamido MEA-Sulfosuccinate, Disodium Sitostereth-14 Sulfosuccinate, Disodium Stearamido MEA-Sulfosuccinate, Disodium Stearyl Sulfosuccinate, Disodium Succinate, Disodium Tallamido MEA-Sulfosuccinate, Disodium Tallowamido MEA-Sulfosuccinate, Disodium Tetrapropenyl Succinate, Disodium Tridecylsulfosuccinate, Disodium Undecylenamido MEA-Sulfosuccinate, Disodium Undecylenamido PEG-2 Sulfosuccinate, Disodium Wheat Germamido MEA-Sulfosuccinate, Disodium Wheat Germamido PEG-2 Sulfosuccinate, Di-TEA-Oleamido PEG-2 Sulfosuccinate, Glyceryl Stearate Succinate, Hydroxypropyl Methylcellulose Acetate/Succinate, Isostearyl Diglyceryl Succinate, Methoxy-PEG-7 Rutinyl Succinate, PEG-20 Hexadecenylsuccinate, PEG-50 Hydrogenated Castor Oil Succinate, PEG-3 PPG-20 Succinate, Potassium Dextrin Octenylsuccinate, Potassium PEG-50 Hydrogenated Castor Oil Succinate, Sodium Bisglycol Ricinosulfosuccinate, Sodium Dextrin Octenylsuccinate, Sodium/MEA Laureth-2 Sulfosuccinate, Sodium PEG-50 Hydrogenated Castor Oil Succinate, Sodium Starch Octenylsuccinate, TEA-Dextrin Octenylsuccinate, TEA-PEG-50 Hydrogenated Castor Oil Succinate.

Ammonium Laureth-6 Carboxylate, Ammonium Laureth-8 Carboxylate, Cetyl C12–15-Pareth-9 Carboxylate, Cetyl PPG-2 Isodeceth-7 Carboxylate, Isopropyl C12–15-Pareth-9 Carboxylate, Isopropyl PPG-2-Isodeceth-7 Carboxylate, Magnesium Laureth-11 Carboxylate, MEA-Laureth-6 Carboxylate, MEA PPG-6 Laureth-7 Carboxylate, MEA-PPG-8-Steareth-7 Carboxylate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Trideceth-n, where n=3, 3, 7, 15, 19, Sodium Capryleth-2 Carboxylate, Sodium Capryleth-9 Carboxylate, Sodium Ceteth-13 Carboxylate, Sodium C9–11 Pareth-6 Carboxylate, Sodium C11–15 Pareth-7 Carboxylate, Sodium C12–13 Pareth-n Carboxylate, where n=6, 8, 12, Sodium C12–15 Pareth-n Carboxylate, where n=6, 7, 8, Sodium C14–15 Pareth-8 Carboxylate, Sodium C12–14 Sec-Pareth-8 Carboxylate, Sodium Isostearth-6 Carboxylate, Sodium Isostearth-11 Carboxylate, Sodium Laureth-3 Carboxylate, Sodium Laureth-n Carboxylate, where n=4, 5, 6, 8, 11, 12, 13, 14, 17, Sodium Lauryl Glycol Carboxylate, Sodium PEG-6 Cocamide Carboxylate, Sodium PEG-8 Cocamide Carboxylate, Sodium PEG-3 Lauramide Carboxylate, Sodium PEG-4 Lauramide Carboxylate, Sodium PEG-7 Olive Oil Carboxylate, Sodium PEG-8 Palm Glycerides Carboxylate, Sodium Trideceth-3 Carboxylate, where n=3, 4, 6, 7, 8, 12, 15, 19, Sodium Undeceth-5 Carboxylate.

Ammonium Cocoyl Sarcosinate, Ammonium Lauroyl Sarcosinate, Isopropyl Lauroyl Sarcosinate, Potassium Cocoyl Sarcosinate, Potassium Lauroyl Sarcosinate, Sodium Cocoyl Sarcosinate, Sodium Lauroyl Sarcosinate, Sodium Myristoyl Sarcosinate, Sodium Palmitoyl Sarcosinate, TEA-Cocoyl Sarcosinate, TEA-Lauroyl Sarcosinate, TEA-Oleoyl Sarcosinate, TEA-Palm Kernel Sarcosinate, Palmitoyl Oligopeptide, Pantothenic Acid Polypeptide, Ammonium Cocoyl Isethionate, Dibromopropamidine Diisethionate, Hexamidine Diisethionate, Sodium Cocoyl Isethionate, Sodium Isethionate, Sodium Lauroyl Isethionate, Sodium Myristoyl Isethionate, Sodium Oleoyl Isethionate.

Aluminum Dicetyl Phosphate, Benzalkonium Cetyl Phosphate, C8–10 Alkyl Ethyl Phosphate, C9–15 Alkyl Phosphate, Ceteareth-2 Phosphate, Ceteareth-4 Phosphate, Ceteareth-5 Phosphate, Ceteareth-10 Phosphate, Ceteth-8 Phosphate, Ceteth-10 Phosphate, Cetyl Phosphate, Cocamidopropyl PG-Dimonium Chloride Phosphate, Cocoyl Hydroxyethylimidazolinium PG-Chloride Phosphate, C6–10 Pareth-4 Phosphate, C12–13 Pareth-10 Phosphate, C12–15 Pareth-n Phosphate, where n=2, 3, 6, 8, 9, 10; C12–16 Pareth-6 Phosphate, DEA-Ceteareth-2 Phosphate, DEA-Cetyl Phosphate, DEA-C8–18 Perfluoroalkylethyl Phosphate, DEA-Oleth-3 Phosphate, DEA Oleth-n Phosphate, where n=5, 10, 20; DEA-Polyperfluoroethoxymethoxy PEG-2 Phosphate, Deceth-9 Phosphate, Deceth-4 Phosphate, Deceth-6 Phosphate, Dicetearetn-10 Phosphate, Dicetyl Phosphate, Di-C12–15 Pareth-n Phosphate, where n=2, 4, 6, 8, 10; Dilaureth-4 Phosphate, Dilaureth-10 Phosphate, Dimyristyl Phosphate, Dioleth-8 Phosphate, Disodium Lauryl Phosphate, Disodium Oleyl Phosphate, Glycereth-26 Phosphate, Hydrogenated Vegetable Glycerides Phosphate, Hydroxyethyl Cetyldimonium Phosphate, Isosteareth-2 Phosphate, Laneth-4 Phosphate, Laureth-n Phosphate, where n=1, 2, 3, 4, 7, 8; Lauryl Phosphate, Linoleamidopropyl PG-Dimonium Chloride Phosphate, Manganese Glycerophosphate, MEA-Dicetearyl Phosphate, Myristamidopropyl Dimethylamine Dimethicone Copolyol Phosphate, Myristamidopropyl Dimethylamine Phosphate, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-n Phosphate, where n=7, 8, 9, 10, 11, 15, 24, Oleth-n Phosphate, where n=2, 3, 4, 5, 10, 20, Oleyl Ethyl Phosphate, Oleyl Phosphate, Palmeth-2 Phosphate, PEG-15 Cocamine Oleate/Phosphate, PEG-26-PPG-30 Phosphate, PEG-45 Stearate Phosphate, Potassium C9–15 Alkyl Phosphate, Potassium C12–13 Alkyl Phosphate, Potassium Cetyl Phosphate, Potassium Deceth-4 Phosphate, Potassium Dihydroxyethyl Cocamine Oxide Phosphate, Potassium Dimethicone Copolyol Panthenyl Phosphate, Potassium Dimethicone Copolyol Phosphate, Potassium Glycerophosphate, Potassium Isostearth-2 Phosphate, Potassium Lauryl Phosphate, Potassium Monofluorophosphate, Potassium Trideceth-6 Phosphate, PPG-21 Butyl Ether Phosphate, PPG-25 Butyl Ether Phosphate, PPG-35 Butyl Ether Phosphate, PPG-5-Ceteth-10 Phosphate, PPG-10 Cetyl Ether Phosphate, Sodium Coco PG-Dimonium Chloride Phosphate, Sodium C13–15 Pareth-8 Butyl Phosphate, Sodium C13–15 Pareth-8 Phosphate, Sodium Dicetearetn-10 Phosphate, Sodium Dihydroxycetyl Phosphate, Sodium Dilaureth-10 Phosphate, Sodium Dioleth-8 Phosphate, Sodium Emuamidopropyl PG-Dimonium Chloride Phosphate, Sodium Glyceryl Oleate Phosphate, Sodium Laureth-4 Phosphate, Sodium Lauroampho PG-Acetate Phosphate, Sodium Lauryl Phosphate, Sodium Milkamidopropyl PG-Dimonium Chloride Phosphate, Sodium Monofluorophosphate, Sodium Oleamidopropyl PG-Dimonium Chloride Phosphate, Sodium Oleth-7 Phosphate, Sodium Oleth-8 Phosphate, Sodium Olivamidopropyl PG-Dimonium Chloride Phosphate, Sodium Steareth-4 Phosphate, Sodium Sunfloweramidopropyl PG-Dimonium Chloride Phosphate, Sodium Zinc Cetyl Phosphate, Stearamidoethyl Diethylamine Phosphate, Stearamidoethyl Ethanolamine Phosphate, Stearamidopropyl PG-Dimonium Chloride Phosphate, Steardimonium Hydroxypropyl PEG-7 Dimethicone Phosphate, Steareth-2 Phosphate, Steareth-3 Phosphate, Stearyl PG-Dimonium Chloride Phosphate, Stearyl Phosphate, TEA-C12–13 Alkyl Phosphate, TEA-Dimethicone Copolyol Phosphate, TEA-Polyphosphatel Tricetearetn-4 Phosphate, Triceteth-5 Phosphate, Tricetyl Phosphate, Tri-C12–15 Pareth-n Phosphate, where n=2, 6, 8, 10, Tricresyl Phosphate, Trideceth-n Phosphate, where n=3, 6, 10, Trilaureth-4 Phosphate, Trilauryl Phosphate, Trioleth-8 Phosphate, Trioleyl Phosphate, Trisodium Lauroampho PG-Acetate Chloride Phosphate, Tristearyl Phosphate.

Non-limiting examples of amphoteric surfactants which may be employed as emulsifiers include: Almondamidopropyl Betaine, Apricotamidopropyl Betaine, Avocadamidopropyl Betaine, Babassuamidopropyl Betaine, Behenamidopropyl Betaine, Behenyl Betaine, Canolamidopropyl Betaine, Capryl/Capramidopropyl Betaine, Cetyl Betaine, Cocamidoethyl Betaine, Cocamidopropyl Betaine, Coco-Betaine, Coco/Oleamidopropyl Betaine, Decyl Betaine, Hydrogenated Tallow Betaine, Isostearamidopropyl Betainem Lauramidopropyl Betaine, Lauryl Betaine, Milkamidopropyl Betaine, Minkamidopropyl Betaine, Myristamidopropyl Betaine, Myristyl Betainem Oleamidopropyl Betaine, Oleyl Betaine, Olivamidopropyl Betaine, Palmamidopropyl Betaine, Palmitamidopropyl Betaine, Palm Kernelamidopropyl Betaine, Polytetrafluoroethylene Acetoxypropyl Betaine, Ricinoleamidopropyl Betaine, Sesamidopropyl Betaine, Soyamidopropyl Betaine, Stearamidopropyl Betaine, Stearyl Betaine, Tallowamidopropyl Betaine, Tallow Betaine, Tallow Dihydroxyethyl Betaine, Undecylenamidopropyl Betaine, Wheat Germamidopropyl Betaine, Almondamidopropylamine Oxide, Babassuamidopropylamine Oxide, Behenamine Oxide, Cocamidopropylamine Oxide, Cocamine Oxide, Decylamine Oxide, Decyltetradecylamine Oxide, Diaminopyrimidine Oxide, Dihydroxyethyl C8–10 Alkoxypropylamine Oxide, Dihydroxyethyl C9–11 Alkoxypropylamine Oxide, Dihydroxyethyl C12–15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Hydrogenated Palm Kernel Amine Oxide, Hydrogenated Tallowamine Oxide, Hydroxyethyl Hydroxypropyl C12–15 Alkoxypropylamine Oxide, Isostearamidopropylamine Oxide, Isostearamidopropyl Morpholine Oxide, Lauramidopropylamine Oxide, Lauramine Oxide, Laurtrimonium Trichlorophenoxide, Milkamidopropyl Amine Oxide, Minkamidopropylamine Oxide, Myristamidopropylamine Oxide, Myristamine Oxide, Myristyl/Cetyl Amine Oxide, Oleamidopropylamine Oxide, Oleamine Oxide, Olivamidopropylamine Oxide, Palmitamidopropylamine Oxide, PPalmitamine Oxide, PEG-3 Lauramine Oxide, Sesamidopropylamine Oxide, Soyamidopropylamine Oxide, Stearamidopropylamine Oxide, Stearamine Oxide, Tallowamidopropylamine Oxide, Tallowamine Oxide, Wheat Germamidopropylamine Oxide.

In one embodiment, the composition comprises about 0.01% to about 10% of an emulsifier component, preferably about 0.01% to about 8%, more preferably 0.1% to about 5%, even more preferably 0.1% to about 5%. Preferably, the emulsifier components form micro emulsions with the polysiloxane components.

In one embodiment, the composition comprises about 0.01% to about 10% of a non-ionic emulsifier, preferably about 0.01% to about 8%, more preferably 0.1% to about 5%, even more preferably 0.1% to about 5%. Preferably, the emulsifier components form micro emulsions with the polysiloxane components.

In one embodiment, the composition comprises about 0.01% to about 5% of a non-ionic emulsifier and at least one of about 0.01% to about 5% of an anionic emulsifier/surfactant and an amphoteric emulsifier/surfactant.

In one embodiment, the composition comprises about 0.01% to about 10% of a polysiloxane component. Preferably, the composition comprises about 0.05% to about 6%, more preferably 0.1% to about 5% of the polysiloxane component.

The popularity of polysiloxane, or dimethicone and dimethicone derivatives, in shampoo compositions originate from their chemical and physical properties. There is a weak intermolecular interaction between polysiloxane molecules and continuing rotation around Si—C and Si—O bonds of the polysiloxane molecules because of the longer Si—C and Si—O than C—C and C—O in regular organic compound. Thus, there is much more space around the silicon atoms and therefore render the polysiloxane excellent spreadbility. Polysiloxane and derivatives also have high refractive index. Furthermore, polysiloxane and derivatives can deliver a smooth feel, detangling and sheen effect to hair.

In one embodiment, the polysiloxane component has the general formula:

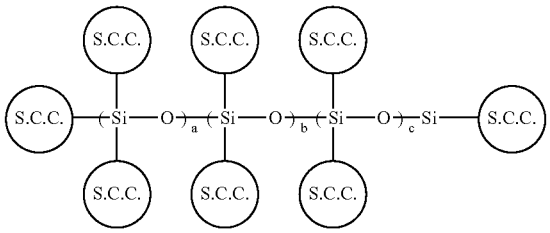

wherein a, b and c are independently 0 to about 1000, preferably 0 to about 500, more preferably 0 to about 100. "s.c.c." as used herein means side chain component. A side chain component is any atom, molecule, polymer or chemical entity which may be covalently attached to the Si of the polysiloxane component. For example, one side chain component may be a hydrocarbon, for example a C1–C10 hydrocarbon or a hydroxide, and another side chain component on the same polysiloxane component may be a hydroxide.

In a preferred embodiment, the polysiloxane component has the general formula:

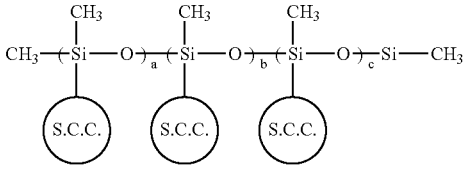

wherein a, b and c are independently 0 to about 50.

In a preferred embodiment, the polysiloxane component comprises about 2 to about 1000 Si, preferably about 4 to about 500 Si, more preferably about 10 to about 300 Si.

In one embodiment, the polysiloxane component comprises at least one side chain component A having the general formula:

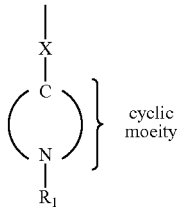

R1 is an H or a C1–C5 hydrocarbon, and X is a C1–C10 hydrocarbon, a heteroatom or

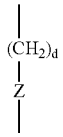

wherein Z is a heteroatom and d is 0 to about 6. Non-limiting examples of heteroatoms useful in this invention includes N, O, S and P. In a preferred embodiment, Z is O (oxygen) and d is about 3.

In one embodiment, the cyclic moiety of the side chain component is saturated. In another embodiment, the cyclic moiety is substituted. For example, the a side chain component A of the polysiloxane component may include the general formula:

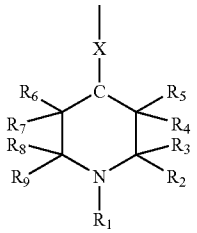

wherein R1, R2, R3, R4, R5, R6, R7, R8 and R9 are independently an H, a C1–C10 hydrocarbon, an ester, carboxyl or a halogen, and X is a C1–C10 hydrocarbon, a heteroatom or

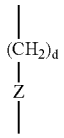

wherein Z is a heteroatom and d is 0 to about 6. Preferably, X is a C1–C5 hydrocarbon or a heteroatom. In one embodiment, X is a heteroatom selected from the group consisting of N, O, Si, P, and S. In a preferred embodiment, R1, R4, R5, R6 and R7 are H's and R2, R3, R8 and R9 are C1 alkyls. Also, in a preferred embodiment, the cyclic moiety is a 5 or 6 member ring.

For example, a side chain component A of a preferred polysiloxane component of this invention has the general formula:

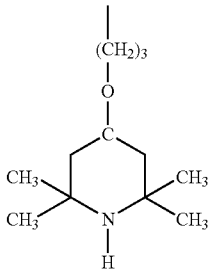

Side chain component A employed in accordance with this invention preferably has a "hindered amine", or a secondary restricted monoamine function group. Preferably, the molecules can be partially protonated at normal shampoo pH range (pH 4–7). The hindered amine functional group is believed to render several beneficial effects. For example, it is believed that the hindered amine polysiloxane (or dimethicone) has more hair or skin affinity and give more conditioning effects. Furthermore, a shampoo comprising a polysiloxane component with a hindered amine functional group is more stable gives more hair softness, smoothness and shine than a shampoo which does not have a hindered amine group.

In one embodiment, the ratio of the Si to the side chain component A in a polysiloxane component is 1:1, preferably 1:0.1, more preferably 1:0.01, even more preferably 1:0.001.

In one embodiment, every other Si of the polysiloxane component has a side chain component A. In another embodiment, every third Si has the side chain component A. In yet another embodiment, every forth, fifth or sixth Si has a side chain component A.

In one embodiment, a polysiloxane component comprises a set of adjacent Si's of the polysiloxane component having side chain component A followed by a set of adjacent Si's having side chain components which are not side chain component A. See, for example, the molecule M below:

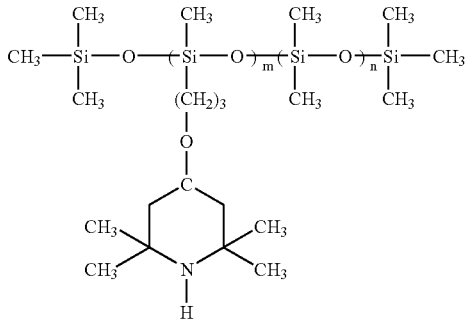

wherein m and n are independently 0 to about 200. See also the molecules identified at www.nicnas.gov.au/publications/CAR/new/NA/NAFULLR/NA08 00FR/NA819FR.pdf as of Nov. 30, 2001, the disclosure of which is incorporated in its entirety herein by reference. In a preferred embodiment, the polysiloxane component comprises propoxytetramethyl piperidinyl dimethicone. Preferably, the propoxytetramethyl piperidinyl dimethicone has a molecular weight of about 10,000 to about 100,000.

In one embodiment, the polysiloxane component has a viscosity in the range of about 1 cps (centistoke) to about 1,000,000 cps (centistoke). Preferably, the polysiloxane component has a viscosity in the range of about 100 cps to about 500,000 cps. More preferably, the polysiloxane component has a viscosity in the range of about 1,000 cps to about 100,000 cps. For example, the polysiloxane component may have a viscosity of about 3,000 cps to about 4,000 cps, preferably about 3,500 cps.

In one embodiment, the polysiloxane component has a viscosity in the range of less than about 1,000,000 cps (centistoke). Preferably, the polysiloxane component has a viscosity of less than about 500,000 cps. More preferably, the polysiloxane component has a viscosity of less than about 100,000 cps. Even more preferably, the polysiloxane component has a viscosity of less than about 10,000 cps.

In one embodiment, the polysiloxane component has a viscosity in the range of more than about 1 cps (centistoke). Preferably, the polysiloxane component has a viscosity of more than about 1,000 cps. More preferably, the polysiloxane component has a viscosity of more than about 3,000 cps. Even more preferably, the poly siloxane component has a viscosity of more than about 10,000 cps.

The amine contents of the polysiloxane components vary with viscosity. The particular value of amine content corresponding to a certain range of viscosity may be determined readily by one of ordinary skill in the art. The amine content of the polysiloxane component may be about 200 to about 40,000 (ppm, N) at about room temperature.

In one embodiment, the polysiloxane component comprises the molecule M and has a viscosity of about 500 to about 6,000 cps at room temperature. In a preferred embodiment, the polysiloxane component comprises the molecule M and has a viscosity of about 1,000 to about 5,000 cps at room temperature. In a more preferred embodiment, the polysiloxane component comprises the molecule M and has a viscosity of about 2,000 to about 4,000 cps at room temperature. In an even more preferred embodiment, the polysiloxane component comprises the molecule M and has a viscosity of about 3,000 to about 4,000 cps, for example about 3,500 cps at room temperature.

In one embodiment, the polysiloxane component is water insoluble. In one embodiment, the polysiloxane component is a colorless, viscous liquid. In one embodiment, the shelf life of the polysiloxane is up to 12 months from date of manufacture.

In one embodiment, the composition comprises about 0.01% to about 10% of an emulsifier component and about 0.01% to about 10% of a polysiloxane component. In one embodiment, the emulsifier component is a mixture of non-ionic emulsifier and an anionic emulsifier (and/or amphoteric emulsifier). For example, the emulsifier component may comprise more than about 90%, more than about 80%, more than about 50%, more than about 30% or more than about 10% of non-ionic emulsifier.

Preferably, the emulsifier component and the polysiloxane component form a micro-emulsion. For example, an emulsifier component comprising an anionic emulsifier (e.g. Capryeth-3) and a non-ionic emulsifier (e.g. Undeceth-5) is added to propoxytetramethyl piperidinyl dimethicone and water to form a micro-emulsion of propoxytetramethyl piperidinyl dimethicone.

The mixture containing the micro-emulsion may be designated as "phase A". Phase A may be added to a detersive component, designated as "phase B", to form a clear composition. A detersive component comprises a chemical or formulation which is effective for cleaning, preferably cleaning hair. For example, the detersive component may comprise one or more of the anionic surfactants or amphoteric surfactants identified herein. In one embodiment, a detersive component may also include emulsifier components, for example the non-ionic emulsifiers above.

In one embodiment, the composition comprises about 5% to about 60% of the detersive component, preferably about 10% to about 50%, more preferably about 20% to about 40%, even more preferably about 20% to about 30%.

A detersive component may further comprise a shampoo additive component. Shampoo additive components include any chemical or formulation that adds to the beneficial qualities of a shampoo. Shampoo additive components include, without limitation, ingredients for boosting foam, protecting the integrity of composition, increasing viscosity, covering the odor of raw material and increasing the attraction of the shampoo. Non-limiting examples of shampoo additive components include alkylamide MEA or alkylamide DEA. Sodium Chloride, preservatives, fragrance and colors.

In one embodiment, the composition comprises about 5% to about 60% (by weight) of the detersive component, 0.01% to about 10% (by weight) of the emulsifier component and about 0.01% to about 10% (by weight) of the polysiloxane component. Preferably, the polysiloxane component comprises a propoxytetramethyl piperidinyl dimethicone.

In one embodiment, the ratio (by weight) of phase a:phase B is about 0.1:99.9, 1:99, 2:98.

We hereby incorporate the disclosures of U.S. Pat. Nos. 5,540,952, 5,277,968 and 6,040,288 in their entirety by reference.

The invention is further illustrated by the following exemplar formulations, which are intended as illustrations only. The thermal and physical stabilities have been tested at both ambient and elevated (40° C.) temperatures. Examples 1–7 are the clear detersive formulations. Examples 1–7 use the pre-emulsified microemulsion in the formula; therefore, it is easy to make stable and clear Propoxytetramethyl Piperidinyl Dimethicone detersive emulsion. The composition is obtained by preparing phase A at 60–70° C. and incorporating silicone phase A into phase B at about 40–50° C. for clear detersive composition. The examples 8–11 are the opaque formulations and were made by directly dispersing the hindered amine silicone into surfactant system. The fragrance, preservatives and color are added and then mixing at 40–50° C. afterwards. The pH for inventive detersive composition should be within 4–7 pH ranges. "q.s." means quantum sufficit, or as much as suffices.

Each of the percentages of the ingredients identified in the Examples below may be individually varied to be higher or lower by about 5% to about 40%, preferably about 5% to about 20%, more preferably about 5% to about 10%, and would still be considered to be within the scope of this invention.

In each of the Examples below, the viscosity of the identified polysiloxane component may be about 1 cps to about 1,000,000 cps (centistoke). For example, the propoxytetramethyl piperidinyl dimethicone (Molecule M) of Example 1 may be about 2,000 cps; the propoxytetramethyl piperidinyl dimethicone (Molecule M) of Example 2 may be about 3,000 cps; the propoxytetramethyl piperidinyl dimethicone (Molecule M) of Example 3 may be about 3,500 cps; the propoxytetramethyl piperidinyl dimethicone (Molecule M) of Example 4 may be about 4,000 cps; the propoxytetramethyl piperidinyl dimethicone (Molecule M) of Example 5 may be about 100,000 cps; the propoxytetramethyl piperidinyl dimethicone (Molecule M) of Example 6 may be about 200,000 cps; the propoxytetramethyl piperidinyl dimethicone (Molecule M) of Example 7 may be about 400,000 cps.

EXAMPLE 1

| | |
|---|---|
| Phase A | |
| Capryleth-3 | 1.12% |
| Undeceth-5 | 1.68% |
| Propoxytetramethyl Piperidinyl Dimethicone | 6.40% |
| Water | 16.2% |
| Phase B | |
| TEA-C12-13 Pareth-3 Sulfate | 16.52% |
| Sodium Cocoamphohydroxypropylsulfonate | 19.72% |
| Cocamidopropyl Betaine | 5.62% |
| Lauramide MEA | 4.36% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 2

| | |
|---|---|
| Phase A | |
| C9-11 Pareth-3 | 0.70% |
| C14-15 Pareth-7 | 0.89% |
| Propoxytetramethyl Piperidinyl Dimethicone | 4.30% |
| Water | 8.78% |
| Phase B | |
| Sodium C9-15 Pareth-3 Sulfate | 12.58% |
| Sodium Oleth Sulfate | 18.72% |
| Coco-Betaine, Coco/Oleamidopropyl Betaine | 4.84% |
| Linoleamide MEA | 4.15% |
| Sodium Chloride | 1.70% |
| Fragrance | q.s. |

-continued

| | |
|---|---|
| Preservatives | q.s. |
| Color | q.s. |
| Water | to 100% |

EXAMPLE 3

| | |
|---|---|
| Phase A | |
| Glycereth-4 | 0.56% |
| Isostearetb-6 | 0.85% |
| Propoxytetramethyl Piperidinyl Dimethicone | 2.88% |
| Water | 8.05% |
| Phase B | |
| Sodium Cocoamphohydroxypropylsulfonate | 17.58% |
| Ammonium Dodecylbenzenesulfonate | 18.72% |
| Myristyl Betaine Oleamidopropyl Betaine | 6.8% |
| Myristamide MEA | 4.53% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 4

| | |
|---|---|
| Phase A | |
| Oleth-3 | 0.48% |
| PPG-2-Ceteth-5 | 0.70% |
| Propoxytetramethyl Piperidinyl Dimethicone | 3.50% |
| Water | 7.01% |
| Phase B | |
| Sodium C12-15 Alkyl Sulfate | 15.58% |
| Potassium Laureth-5 Carboxylate | 18.72% |
| Behenamide MEA | 4.26% |
| Soyamidopropyl Betaine | 5.9% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 5

| | |
|---|---|
| Phase A | |
| Ceteth-3 | 0.24% |
| Ceteareth-6 | 0.30% |
| Propoxytetramethyl Piperidinyl Dimethicone | 1.50% |
| Water | 3.0% |
| Phase B | |
| Sodium C12-15 Alkyl Sulfate | 13.58% |
| Sodium C12-15 Pareth Sulfate | 18.72% |
| Tallowamidopropylamine Oxide | 4.3% |
| Cocamide MEA | 3.56% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 6

| | |
|---|---|
| Phase A | |
| Deceth-3 | 0.28% |
| Trideceth-3 | 0.42% |
| Propoxytetramethyl Piperidinyl Dimethicone | 1.40% |
| Water | 4.20% |
| Phase B | |
| Sodium C9-15 Pareth-3 Sulfate | 12.58% |
| Sodium C12-13 Alkyl Sulfate | 18.72% |
| Cocamide MEA | 3.37% |
| Apricotamidopropyl Betaine | 4.4% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 7

| | |
|---|---|
| Phase A | |
| Undeceth-3 | 0.06% |
| C14-15 Pareth-7 | 0.075% |
| Propoxytetramethyl Piperidinyl Dimethicone | 0.40% |
| Water | 0.75% |
| Phase B | |
| Sodium Oleth Sulfate | 12.58% |
| Sodium Myristyl Sulfate | 18.72% |
| Ricinoleamidopropyl Betaine | 3.95% |
| Cocamide MEA | 3.84% |
| Disodium EDTA | 0.05% |
| Fragrance | q.s. |
| Sodium Chloride | 1.70% |
| Preservatives | q.s. |
| Color | q.s. |
| Water | to 100% |

EXAMPLE 8

| | |
|---|---|
| Sodium Trideceth Sulfate | 16.53% |
| TEA-C12-13 Pareth-3 Sulfate | 18.72% |
| Lauramidopropylamine Oxide | 3.58% |
| Cocamide MEA | 3.84% |
| Disodium EDTA | 0.05% |
| Glycereth-4 | 0.36% |
| Oleth-9 | 0.45% |
| Propoxytetramethyl Piperidinyl Dimethicone | 2.25% |
| Fragrance | q.s. |
| Preservatives | q.s. |
| Sodium Chloride | 1.70% |
| Color | q.s. |
| Water | to 100% |

EXAMPLE 9

| | |
|---|---|
| Ammonium Dodecylbenzenesulfonate | 12.58% |
| Potassium Dodecylbenzenesulfonate | 18.72% |
| Isostearetb-4 | 0.74% |
| Trideceth 7 | 1.26% |
| Propoxytetramethyl Piperidinyl Dimethicone | 4.20% |

-continued

| | |
|---|---|
| Cocoamidopropylamine Oxide | 4.56% |
| Cocamide MEA | 3.84% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 10

| | |
|---|---|
| Sodium Cocoamphohydroxypropylsulfonate | 19.21% |
| Ammonium Lauryl Sulfosuccinate, | 18.72% |
| Cocamide MEA | 3.84% |
| Myristamide MEA | 2.89% |
| Trideceth 4 | 1.40% |
| C14-15 Pareth-6 | 2.10% |
| Propoxytetramethyl Piperidinyl Dimethicone | 7.10% |
| Disodium EDTA | 0.05% |
| Fragrance | q.s. |
| Preservatives | q.s. |
| Sodium Chloride | 1.70% |
| Color | q.s. |
| Water | to 100% |

EXAMPLE 11

| | |
|---|---|
| Potassium Laureth-5 Carboxylate, | 22.58% |
| Disodium Lauramido MEA-Sulfosuccinate | 18.02% |
| Myristamide MEA | 3.47% |
| Cocamide MEA | 3.84% |
| Trideceth 3 | 1.20% |
| Trideceth 6 | 1.50% |
| Propoxytetramethyl Piperidinyl Dimethicone | 8.00% |
| Disodium EDTA | 0.05% |
| Fragrance | q.s. |
| Preservatives | q.s. |
| Sodium Chloride | 1.70% |
| Color | q.s. |
| Water | to 100% |

While this invention has been described with respect to various specific examples and embodiments, it is to be understood that the invention is not limited thereto and that it can be variously practiced with the scope of the following claims.

What is claimed is:

1. A hair shampoo composition comprising an effective amount of a detersive component, an effective amount of an emulsifier component and a polysiloxane component in an amount effective as a hair conditioner, the hair shampoo composition being clear, the polysiloxane component comprises at least one side chain component A having the general formula:

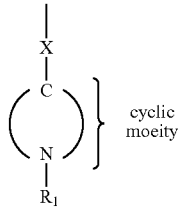

$R_1$ is an H, OH or a C1–C5 hydrocarbon; X is a C1–C10 hydrocarbon, a heteroatom or

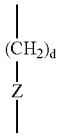

Z is a heteroatom and d is 0 to about 6, the polysiloxane component has a viscosity of about 1 centistoke to about 1,000,000 centistoke.

2. The composition of claim 1 comprising about 5% to about 60% of the detersive component, about 0.01% to about 10% of the emulsifier component, and about 0.01% to about 10% of the polysiloxane component.

3. The composition of claim 1 wherein the detersive component comprises a surfactant selected from the group consisting of an anionic surfactant, an amphoteric surfactant and a mixture thereof.

4. The composition of claim 1 wherein the emulsifier component comprises a non-ionic emulsifier.

5. A clear hair shampoo composition comprising:

(a) about 0.01% to about 10% of an emulsifier component; and (b) about 0.01% to about 10% of a polysiloxane component, the polysiloxane component comprises a side chain component A having the general formula;

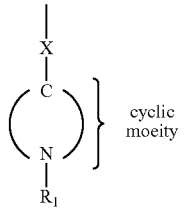

$R_1$ is an H or a C1–C5 hydrocarbon; X is a C1–C10 hydrocarbon, a heteroatom or

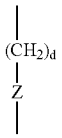

Z is a heteroatom and d is 0 to about 6, the polysiloxane component has a viscosity of about 1 centistoke to about 1,000,000 centistoke and is effective as a hair conditioner in a hair shampoo, wherein the composition is formulated as a clear hair shampoo composition.

6. The composition of claim 5 wherein the polysiloxane component has a viscosity of about 1,000 centistoke to about 500,000 centistoke.

7. The composition of claim 5 wherein the polysiloxane component has a viscosity of about 1,000 centistoke to about 10,000 centistoke.

8. The composition of claim 5 wherein the polysiloxane component has a viscosity of about 1,000 centistoke to about 5,000 centistoke.

9. The composition of claim 5 wherein the polysiloxane component has a viscosity of about 2,000 centistoke to about 4,000 centistoke.

10. The composition of claim 5 wherein the emulsifier component comprises:

about 0.01% to about 5% of an anionic or an amphoteric surfactant; and about 0.01% to about 5% of a non-ionic emulsifier.

11. The composition of claim 5 in the side chain component A has the general formula:

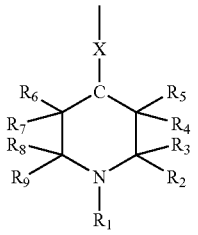

wherein R1, R2, R3, R4, R5, R6, R7, R8 and R9 are independently an H, a C1–C10 hydrocarbon, an ester, carboxyl or a halogen; X is a C1–C10 hydrocarbon, a heteroatom or

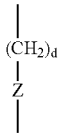

Z is a heteroatom and d is 0 to about 6.

12. The composition of claim 5 wherein the side chain component A has the general formula:

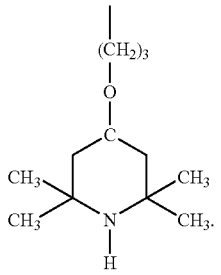

13. The composition of claim 5 further comprising a detersive component.

14. The composition of claim 5 further comprising about 5% to about 60% of a detersive component.

15. The composition of claim 5 further comprising a shampoo additive component.

16. A method of making a clear hair shampoo composition comprising:

combining (1) a microemulsion comprising an effective amount of an emulsifier component, a polysiloxane component in an amount effective as a hair conditioner in a hair shampoo and water and (2) an effective amount of a detersive component at conditions effective to form a clear hair shampoo composition, wherein the polysiloxane component comprises at least one side chain component A having the general formula:

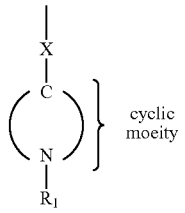

$R_1$ is an H, OH or a C1–C5 hydrocarbon; X is a C1–C10 hydrocarbon, a heteroatom or

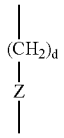

Z is a heteroatom and d is 0 to about 6, the polysiloxane component has a viscosity of about 1 centistoke to about 1,000,000 centistoke.

17. The method of claim 16 wherein the side chain component A has the general formula:

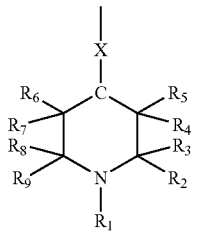

wherein $R_1$, $R_2$, $R_3$, $R_4$, $R_5$, $R_6$, $R_7$, $R_8$ and $R_9$ are independently an H, a C1–C10 hydrocarbon, an ester, carboxyl or a halogen; X is a C1–C10 hydrocarbon, a heteroatom or

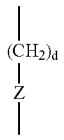

Z is a heteroatom and d is 0 to about 6.

18. The method of claim 16 wherein the side chain component A has the general formula:

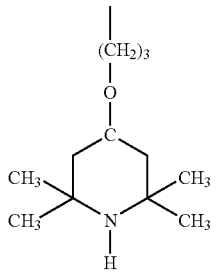

19. The method of claim 16 wherein the polysiloxane component has a viscosity of about 1 centistoke to about 1,000,000 centistoke.

*20. A method of cleansing or conditioning hair comprising applying to said hair a composition comprising an effective amount of an emulsifier component and a polysiloxane component in an amount effective as a hair conditioner, the polysiloxane component comprises at least one side chain component A having the general formula:*

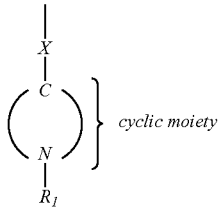

*$R_1$ is an H, OH or a $C_1$-$C_5$ hydrocarbon; X is a $C_1$-$C_{10}$ hydrocarbon, a heteroatom or*

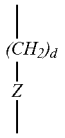

*Z is a heteroatom and d is 0 to about 6, the polysiloxane component has a viscosity of about 1 centistoke to about 1,000,000 centistoke.*

*21. The method of claim 20 wherein the composition comprises an effective amount of a surfactant component.*

*22. The method of claim 21 wherein the surfactant component is selected from the group consisting of anionic surfactants, amphoteric surfactants and mixtures thereof.*

*23. The method of claim 21 wherein the composition comprises about 5% to about 60% by weight of the surfactant component.*

*24. The method of claim 20 wherein the composition comprises an effective amount of a color component.*

*25. The method of claim 20 wherein the composition is clear.*

*26. The method of claim 20 wherein the composition is formulated as a hair shampoo composition.*

*27. The method of claim 20 wherein the composiion has enhanced skin affinity as compared to a similar composition lacking said polysiloxane.*

*28. The method of claim 21 wherein the composition is formulated as a composition effective for cleaning skin.*

*29. The method of claim 20 wherein the composition contains a non-ionic emulsifier.*

*30. The method of claim 20 wherein the side chain component A included in the composition has the general formula:*

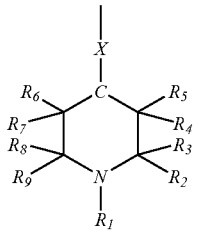

*wherein R1, R2, R3, R4, R5, R6, R7, R8 and R9 are independently an H, a $C_1$-$C_{10}$ hydrocarbon, an ester, carboxyl or a halogen; X is a $C_1$-$C_{10}$ hydrocarbon, a heteroatom or*

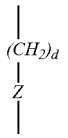

*Z is a heteroatom and d is 0 to about 6.*

*31. The method of claim 20 wherein the side chain component A included in the composition has the general formula:*

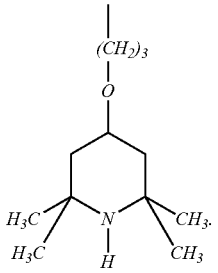

*32. The method of claim 20 wherein the composition comprises about 0.01% to about 10% by weight of the emulsifier component.*

*33. The method of claim 20 wherein the composition comprises about 0.01% to about 10% by weight of the polysiloxane component.*

*34. The method of claim 20 wherein the polysiloxane component of the composition has a viscosity of about 1 centistokes to about 1,000,000 centistokes.*

*35. The method of claim 20 wherein the polysiloxane component of the composition has a viscosity of about 1,000 centistoke to about 500,555 centistoke.*

*36. The method of claim 20 wherein the polysiloxane component of the composition has a viscosity of about 1,000 centistoke to about 10,000 centistoke.*

*37. The method of claim 20 wherein the polysiloxane component of the composition has a viscosity of about 1,000 centistoke to about 5,000 centistokes.*

*38. The method of claim 20 wherein the polysiloxane component of the composition has a viscosity of about 2,000 centistoke to about 4,000 centistoke.*

* * * * *